United States Patent [19]

Givens et al.

[11] 4,079,095

[45] Mar. 14, 1978

[54] MANUFACTURE OF LIGHT OLEFINS

[75] Inventors: Edwin N. Givens, Pitman; Charles J. Plank, Woodbury; Edward J. Rosinski, Pedrick Town, all of N.J.

[73] Assignee: Mobil Oil Corporation, New York, N.Y.

[21] Appl. No.: 738,772

[22] Filed: Nov. 4, 1976

[51] Int. Cl.$^2$ .............................. C07C 1/24
[52] U.S. Cl. .................................... 260/682
[58] Field of Search ........................ 260/682

[56] References Cited

U.S. PATENT DOCUMENTS

| 3,240,697 | 3/1966 | Miale et al. | 260/682 |
| 3,894,102 | 7/1975 | Chang et al. | 260/682 |
| 3,979,472 | 9/1976 | Butter | 260/682 |

Primary Examiner—Delbert E. Gantz
Assistant Examiner—C. E. Spresser
Attorney, Agent, or Firm—Charles A. Huggett; Raymond W. Barclay

[57] ABSTRACT

A catalytic process is provided for converting an organic charge consisting essentially of methanol, dimethyl ether or mixtures thereof together with at least about 0.25 moles of water per mole of said organic charge to a hydrocarbon product rich in ethylene and propylene by contact, under conversion conditions, with a catalyst comprising a crystalline aluminosilicate zeolite of the erionite-offretite family.

19 Claims, No Drawings

MANUFACTURE OF LIGHT OLEFINS

CROSS REFERENCES TO RELATED APPLICATIONS

ZSM-34 as a new crystalline aluminosilicate zeolite, its method of preparation and hydrocarbon conversion in the presence thereof are described in copending application Ser. No. 738771, filed concurrently herewith.

BACKGROUND OF THE INVENTION

1. Field of the Invention

This invention relates to a process for the conversion of a mixture of (1) methanol, dimethyl ether or mixtures thereof and (2) water to light olefins in the presence of a crystalline aluminosilicate zeolite of the erionite-offretite family.

2. Description of the Prior Art

U.S. Pat. No. 3,036,134 to Mattox discloses conversion of methanol to a reaction product containing water and dimethyl ether in the presence of a sodium or calcium crystalline aluminosilicate zeolite catalyst.

U.S. Pat. No. 3,529,033 to Frilette and Weisz discloses dehydration of a normal alkanol of three to six carbon atoms to an olefin, utilizing a sodium or calcium crystalline aluminosilicate zeolite catalyst having uniform interstitial dimensions sufficiently large to admit the alkanol charge and to permit egress therefrom of the olefin product.

The prior art, typified by the above patents, has, neither disclosed nor recognized the advantages of a process for selectively converting a mixture of (1) methanol, dimethyl ether or mixtures thereof and (2) water to $C_2$–$C_3$ olefins utilizing the crystalline aluminosilicate zeolite catalyst described herein.

As those in the art are aware, a remarkable growth in the production of synthetic fibers, platics and rubber has taken place in recent decades. Their growth, to a very large extent, has been supported and encouraged by an expanding supply of inexpensive petroleum raw materials such as ethylene and propylene. Increasing demand for these light olefins has, from time to time, led to periods of shortage, either due to a diminished supply of suitable feedstocks or to limited processing capacity. In any event, it is considered highly desirable to provide efficient means for converting raw materials other than petroleum to light olefins.

SUMMARY OF THE INVENTION

In accordance with the present invention, there has been discovered a process which selectively produces valuable light olefinic hydrocarbons. The present process involves conversion of an organic charge consisting essentially of methanol, dimethyl ether or mixtures thereof together with at least about 0.25 moles of water per mole of organic charge by contact at elevated temperatures with a catalyst comprising a crystalline aluminosilicate zeolite of the erionite-offretite family.

It has been found that use of such zeolite catalysts in combination with added water afford a substantially higher efficiency and selectivity for ethylene and propylene production over corresponding use of similar crystalline aluminosilicate zeolites in the absence of added water. It has further been found utilizing the specified crystalline aluminosilicate zeolite catalyst described herein that the $C_2$–$C_3$ olefin content of the reaction product preferably constitutes a major proportion of such reaction product. The latter is substantially devoid of aromatic hydrocarbon content and contains, as a result of employing the specified catalyst, less than 20 weight percent, and preferably not more than 10 weight percent, of methane.

The methanol feedstock may be manufactured from synthesis gas, i.e., a mixture of CO and $H_2$, from coal or may be produced by fermentation.

The present process comprises conversion of methanol, dimethyl ether or mixtures thereof together with added water in the presence of the specified catalyst at a temperature between about 500° F. and about 1000° F. at a pressure between about 0.1 and about 30 atmospheres and preferably at atmospheric pressure utilizing a weight hourly space velocity (WHSV) between about 0.1 and about 30 and preferably between about 1 and about 10, said operating conditions being selected to produce olefins boiling below $C_5$ hydrocarbons. The WHSV is based upon the weight of zeolite in the catalyst composition. The effluent is separated and distilled to remove the desired products of light olefinic hydrocarbons. Any unreacted charge may be recycled for further reaction.

DESCRIPTION OF SPECIFIC EMBODIMENTS

It is contemplated that an organic charge consisting essentially of methyl alcohol, dimethyl ether or mixtures thereof, together with at least about 0.25 moles of added water per mole of organic charge may be used as feed to the process of this invention. Such feed, in accordance with this invention, is brought into contact, under the aforenoted conversion conditions, with a bed comprising particle-form catalyst containing a crystalline aluminosilicate zeolite of the erionite-offretite family. Included within this group of zeolites is erionite, both synthetic and natural, offretite, both synthetic and natural, zeolite T and zeolite ZSM-34. These zeolites have the common characteristic of possessing X-ray diffraction patterns which are substantially the same or similar to those of erionite and offretite.

Zeolite T is described in U.S. Pat. No. 2,950,952. Zeolite ZSM-34 and its synthesis are subject matter of copending application Ser. No. 738771 filed Nov. 4, 1976, the contents of which are incorporated herein by reference. ZSM-34 is a unique crystalline aluminosilicate zeolite, belonging to the erionite-offretite family, having the composition, as synthesized, and after drying of:

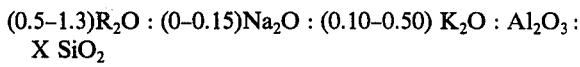

$(0.5$–$1.3)R_2O : (0$–$0.15)Na_2O : (0.10$–$0.50) K_2O : Al_2O_3 : X\ SiO_2$ where R is the organic nitrogen-containing cation derived from choline $[(CH_3)_3 NCH_2CH_2OH]$ and X is 8 to 50, preferably 8 to 30 and still more preferably 8 to 20. This zeolite, unlike other members of the erionite-offretite family, appears to have a tabular morphology and the capability, after calcination at 1000° F. for at least a period of time to remove the organic cation of sorbing at least 9.5 weight percent of n-hexane, at ambient temperature and a n-hexane pressure of 20 mm. which is higher than that for any other known offretite or erionite.

ZSM-34 is characterized by an X-ray powder diffraction pattern as set forth in Table 1 below:

TABLE 1

| 2θ | D(A) | Relative Intensity |
|---|---|---|
| 7.68 | 11.5 ± .2 | VS |
| 9.62 | 9.2 ± .2 | W |
| 11.67 | 7.58 ± .15 | M |
| 13.39 | 6.61 ± .13 | S |
| 14.01 | 6.32 ± .12 | W |
| 15.46 | 5.73 ± .11 | M |
| 16.57 | 5.35 ± .10 | W |
| 17.81 | 4.98 ± .10 | W |
| 19.42 | 4.57 ± .09 | S-VS |
| 20.56 | 4.32 ± .08 | VS |
| 21.36 | 4.16 ± .08 | W |
| 23.35 | 3.81 ± .07 | S-VS |
| 23.79 | 3.74 ± .07 | VS |
| 24.80 | 3.59 ± .07 | S-VS |
| 27.02 | 3.30 ± .06 | M-S |
| 28.33 | 3.15 ± .06 | M |
| 30.62 | 2.92 ± .05 | W |
| 31.41 | 2.85 ± .05 | VS |
| 31.93 | 2.80 ± .05 | W |
| 33.50 | 2.67 ± .05 | W |
| 35.68 | 2.52 ± .05 | W |
| 36.15 | 2.48 ± .05 | W-M |
| 38.30 | 2.35 ± .04 | W |
| 39.49 | 2.28 ± .04 | W |

The intensity in the above Table is expressed as follows:

| Relative Intensity | $100 I/I_o$ |
|---|---|
| VS (Very Strong) | 60–100 |
| S (Strong) | 40–60 |
| M (Medium) | 20–40 |
| W (Weak) | 0–20 |

This zeolite, as synthesized, may be calcined to remove the organic constituent ($R_2O$) and/or ion exchanged to replace the alkali metal ions with hydrogen ion precursor and/or other metal ions, particularly metals from Groups IB, II, III, VIIB, VIII and the rare earth metals with only minor changes in the X-ray characterization and sorption properties. The calcined and ion exchanged product is catalytically active ZSM-34 useful in the process of this invention.

ZSM-34 can be suitably synthesized by preparing a gel reaction mixture having a composition, in terms of mole ratios of oxides, falling within the following ranges:

| | Broad | Preferred |
|---|---|---|
| $SiO_2/Al_2O_3$ = | 10–70 | 10–55 |
| $OH^-/SiO_2$ = | 0.3–1.0 | 0.3–0.8 |
| $H_2O/OH^-$ = | 20–100 | 20–80 |
| $K_2O/M_2O$ = | 0.1–1.0 | 0.1–1.0 |
| $R^+/R^+ + M^+$ = | 0.1–0.8 | 0.1–0.5 | where $R^+$ is choline [$(CH_3)_3$·N—$CH_2CH_2OH$] and M is Na+K and maintaining the mixture until crystals of the zeolite are formed. $OH^-$ is calculated from inorganic base not neutralized by any added mineral acid or acid salt. Resulting zeolite crystals are separated and recovered. Typical reaction conditions consist of heating the foregoing reaction mixture to a temperature of from about 80° C. to about 175° C. for a period of time of from about 12 hours to 200 days. A more preferred temperature range is from about 90° to about 160° C. with the amount of time at a temperature in such range being from about 12 hours to 50 days.

The resulting crystalline product is separated from the mother liquor by filtration, water washing and drying, e.g., at 230° F for from 4 to 48 hours. Milder conditions may be employed, if desired, e.g., room temperature under vacuum.

ZSM-34, when employed either as an absorbent or as a catalyst in a hydrocarbon conversion process, should be at least partially dehydrated and the organic cation at least partially removed. This can be done by heating to a temperature in the range of 200° to 750° C. in an atmosphere such as air, nitrogen, etc. and at atmospheric or sub-atmospheric pressure for between 1 and 48 hours. Dehydration can also be performed at lower temperatures merely by placing the catalyst in a vacuum, but a longer time is required to obtain a sufficient amount of dehydration.

The composition of ZSM-34 can be prepared utilizing materials which supply the appropriate oxides. Such compositions include, for example, sodium aluminate, alumina, sodium silicate, silica hydrosol, silica gel, silicic acid, sodium hydroxide, aluminum sulfate, potassium hydroxide, potassium silicate, and choline. It will be understood that each oxide component utilized in the reaction mixture for preparing ZSM-34 can be supplied by one or more initial reactants and they can be mixed together in any order. The reaction mixture can be prepared either batchwise or continuously. Crystal size and crystallization time of the ZSM-34 composition will vary with the nature of the reaction mixture employed.

As aforenoted, other erionite-offretite type zeolites, while less preferred than ZSM-34, may be employed in the process described herein. Such zeolites include erionite and offretite, which may be either in the naturally occurring form or synthetic. In the latter form, the cation may comprise an alkali or alkaline earth, or may be an organic cation, e.g., tetramethylammonium or benzyl tetramethylammonium. The latter, upon calcination are converted to the hydrogen form.

The zeolites useful in the conversion process of this invention generally have at least 10 percent of the cationic sites thereof occupied by ions other than alkali or alkaline earth metals. Typical but non-limiting replacing ions include ammonium, hydrogen, rare earth, zinc, copper and aluminum. Of this group, particular preference is accorded ammonium, hydrogen, rare earth or combinations thereof. In a preferred embodiment, the zeolites are converted to the predominately hydrogen form, either by calcination of an organic cation form, as indicated above and/or by replacement of the alkali metal or other ion originally present with hydrogen ion precursors, e.g., ammonium ions, which upon calcination yield the hydrogen form. This exchange is conveniently carried out by contact of the zeolite with an ammonium salt solution, e.g., ammonium chloride, utilizing well known ion exchange techniques. The extent of replacement is such as to produce a zeolite material in which at least 50 percent of the cationic sites are occupied by hydrogen ions.

In practicing the desired conversion process, it may be desirable to incorporate the above-described crystalline aluminosilicate zeolites in another material resistant to the temperature and other conditions employed in the process. Such matrix materials include synthetic or naturally occurring substances as well as inorganic materials such as clay, silica and/or metal oxides. The latter may be either naturally occuring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the small pore zeolites employed herein may be compounded with a porous matrix material, such as alumina, silica-alumina, silica-magnesia, silica-zirconia, silica-thoria, silica-beryllia, silica-titania, as well as ternary combinations, such as silica-alumina-thoria, silica-alumina-zirconia, silica-alumina-magnesia and silica-magnesia-zirconia. The matrix may be in the form of a cogel. The relative proportions of finely divided zeolite and inorganic oxide gel matrix may vary widely with the zeolite content ranging from between about 1 to about 99 percent by weight and more usually in the range of about 5 to about 80 percent by weight of the composite.

In the process of converting methyl alcohol and/or dimethyl ether to hydrocarbons, water is a major product of reaction. In accordance with the present invention, it has been found that the addition of water to the initial methanol and/or dimethyl ether feed serves to enhance the selective production of $C_2$ and $C_3$ olefins. Thus, it has been found that the addition of water to the noted feed is particularly beneficial in directing the conversion toward light olefin ($C_2$ and $C_3$) production and away from the formation of $C_4^+$ hydrocarbons. In so doing, the initial presence of water in the reaction mixture, also has been found to lengthen the cycle life of the catalyst. Without being limited by any theory, it is believed that this is due to a decrease in the rate of coke formation.

The amount of water added along with the organic charge of methanol and/or dimethyl ether is generally at least about 0.25 moles of water per mole of the organic charge. Preferably, the amount of water added is greater than about 0.5 moles of water per mole of organic charge. The amount of water initially added to the organic charge usually will not exceed about 40 moles per mole of said charge.

The process of this invention is conducted such that methyl alcohol and/or dimethyl ether conversion is carried out in the vapor phase by contact in a reaction zone, such as for example, a fixed, fluidized or moving bed of catalyst, under effective conversion conditions. Such conditions include an operating temperature between about 500° F. and about 1000° F., a pressure between about 0.1 and about 30 atmospheres and preferably atmospheric pressure and a weight hourly space velocity between about 0.1 and about 30 and preferably between about 1 and about 10. Carrier gases or diluents may be injected into the reaction zone such as, for example, hydrogen or nitrogen.

The methyl alcohol and/or dimethyl ether conversion process described herein may be carried out as a batch-type, semi-continuous or continuous operation utilizing a fixed, fluidized or moving bed catalyst system. A preferred embodiment entails use of a catalyst zone wherein the alcohol or ether charge together with added water is passed concurrently or countercurrently through a fluidized or moving bed of particle-form catalyst. The latter after use is conducted to a regeneration zone wherein coke is burned from the catalyst in an oxygen-containing atmosphere, e.g., air, at an elevated temperature, after which the regenerated catalyst is recycled to the conversion zone for further contact with the alcohol and/or ether water feed.

The product stream in the process of the invention contains steam and a hydrocarbon mixture of paraffins and olefins, substantially devoid of aromatics. This mixture is particularly rich in light olefins, i.e., ethylene and propylene. Generally, a major fraction of the total olefins is ethylene plus propylene with the ethylene contact of the product exceeding the propylene content. Thus, the predominant hydrocarbon product constitutes valuable petrochemicals. The steam and hydrocarbon products maybe separated from one another by methods well known in the art.

In a preferred embodiment of the invention, the unconverted methanol and/or dimethyl ether, as well as at least part of the water in the product, are recycled to the reaction zone.

The following examples will serve to illustrate the process of this invention without limiting the same.

EXAMPLE 1

ZSM-34 was prepared by interacting the following solutions:

A. Caustic Aluminate
68.89 grams sodium aluminate (20 wt.% Na, 43.1 wt.% $Al_2O_3$, Balance $H_2O$
29.28 grams NaOH (77.5 wt.% $Na_2O$)
26.4 grams KOH 86.4% KOH
540 grams $H_2O$ B. Silica Solution
780 grams Colloidal Silica sol (30 Wt. % $SiO_2$)

C. Choline Chloride
228 grams

These were mixed together in a 2 liter autoclave adding solution C to solution A and then adding solution B followed by a 15 minute continuous mixing. The autoclave was then sealed, pressure-tested and then heated to and held at 300° F. for 8 days. The contents were stirred continuously during the 8 days crystallization period.

The autoclave and its contents were cooled to room temperature and the crystalline product was filtered and washed. On analysis the product was found to contain:

Na, wt %: 0.68
K, wt %: 3.59
$Al_2O_3$ wt %: 13.5
$SiO_2$, wt %: 78.5
N, wt %: 2.5

The resulting ZSM-34 product had the following molar composition:

0.54 $R_2O$: 0.11 $Na_2O$ : 0.35 $K_2O$ : $Al_2O_3$ : 9.87 $SiO_2$

The adsorption data for the product after calcining in air at 1000° F. for 10 hours was as follows:
Cyclohexane, wt %: 3.5
n-Hexane, wt %: 9.6
$H_2O$, wt %: 19.7

A sample of the calcined alkali ZSM-34 was further processed by contacting with a 10 wt % $NH_4Cl$ solution for 1 hour at about 185° F. using 10 ml. of solution for each gram of ZSM-34. A total of four contacts were made at these conditions followed by final filtration and water washing essentially free of chloride ion.

The product was dried at 230° F. and calcined for 10 hours at 1000° F. The residual alkali content as Na was 0.035 wt % while the residual K content was 1.47 wt %. This product had a surface area of 517 m²/g and the following sorption capacity:

Cyclohexane, wt %: 2.6
n-Hexane, wt %: 10.0
H₂O, wt %: 18.7

EXAMPLE 2

A feed comprised of 30 wt % methanol and 70% water was passed over 2.0 grams of the catalyst of Example 1 at a rate of 7.7 ml per hour. The catalyst contained in a 15 mm outer diameter tubular glass reactor, had an axial bed length of 1⅝ inches. The catalyst was air calcined in place at 1000° F. for one hour with an air flow of 10 cc/min. Nitrogen at a rate of 10 cc/min was passed over the bed for 10 minutes while the temperature dropped to 700° F. The run conditions, temperature profile of the bed and the product analysis of reactor effluent samples taken at four different intervals during the run are set forth in Table 2 below.

TABLE 2

| Hours on Stream | | 1-2 | 4.5-5.5 | 7-8 | 11-12 |
|---|---|---|---|---|---|
| Temp. ° F. (inches from top) | 0 | 655 | 645 | 638 | 654 |
| | ½ | 693 | 682 | 687 | 693 |
| | 1 | 700 | 693 | 702 | 705 |
| | 1½ | 705 | 706 | 723 | 725 |
| | 1⅞ | 706 | 716 | 730 | 735 |
| Temp. Profile, Hrs. | | 2 | 5.5 | 8 | 12 |
| Calculations On Recovered: | | | | | |
| WHSV Total | | 3.6 | 3.6 | 2.9 | 2.9 |
| MeOH | | 0.86 | 1.0 | 0.81 | 0.76 |
| Water | | 2.7 | 2.6 | 2.1 | 2.1 |
| Converted MeOH (wt.%) | | 96.0 | 65.4 | 37.1 | 33.8 |
| Product (excludes unreacted charge) wt. % | | | | | |
| DME | | 1.9 | 19.3 | 47.2 | 57.2 |
| Water | | 55.5 | 48.7 | 37.8 | 33.8 |
| HC Phase | | 42.6 | 32.0 | 15.0 | 8.9 |
| HC Distribution (wt. %) | | | | | |
| $C_1$ | | 1.8 | 3.0 | 4.9 | 7.5 |
| $C_2=$ | | 48.8 | 56.0 | 52.9 | 53.7 |
| $C_2$ | | 1.8 | 0.4 | 0 | 0 |
| $C_3=$ | | 26.8 | 27.2 | 27.7 | 25.8 |
| $C_3$ | | 7.1 | 0 | 0 | 0 |
| $C_4=$ | | 7.8 | 6.5 | 6.5 | 6.0 |
| $C_4$ | | 3.3 | 4.7 | 3.6 | 4.5 |
| $C_5$ | | 2.6 | 2.2 | 4.5 | 2.6 |

EXAMPLE 3

ZSM-34 was prepared by interacting the following solutions:

A. Caustic Aluminate Solution
  22.96 grams NaAlO₂ (43.1 wt % Al₂O₃, 33.1 wt % Na₂O, 23.8 wt % H₂O)
  9.76 grams NaOH (97.5%)
  8.8 grams KOH (86.4%)
  180 grams H₂O
B. Colloidal Silica
  260 grams (30 wt % SiO₂)
C. Choline Chloride
  76 grams These solutions were mixed together by adding C to A then adding B and mixing for 15 minutes. The mixture was transferred to a polypropylene container and reacted at 210° F for 32 days yielding a zeolite identified as ZSM-34.

A sample of the above alkali zeolite after filtering, washing, and drying had the following molar composition:

0.07 Na₂O : 0.36 K₂O : 0.67 R₂O : Al₂O₃ : 10.2 SiO₂ where R is the organic ion derived from choline chloride.

The adsorption capacity for a sample of the above product calcined (16 hrs. at 1000° F) was:

Cyclohexane, wt %: 4.9
n-Hexane, wt %: 10.3
H₂O, wt %: 20.9

The surface area for the calcined sample was 524 m²/g.

Another sample of the above alkali product was processed by calcining for 10 hours at 1000° F and exchanged with a 10 wt % NH₄Cl solution at 185° F employing 5 one hour contacts. After the final contact the exchanged product was filtered, water washed, dried at 230° F, pelleted and sized 14-25 mesh and calcined for 10 hours at 1000° F in air.

EXAMPLE 4

Methanol at a rate of 4.0 ml/hour was passed over a 1 gram sample of the catalyst of Example 3 at a temperature of 700° F. The effluent stream from the reactor was collected between 1 and 2 hours on stream. The run conditions and product analyses are shown in Table 3.

EXAMPLE 5

Addition of steam as a diluent improved the selectivity for ethylene. A charge solution comprised of 30% by weight of methyl alcohol and 70% by weight of water was passed over 1.0 gram of the catalyst from Example 4 at a rate of 3.6 grams per hour. The run was made at a nominal 700° F. and atmospheric pressure. The catalyst bed had an axial bed length of 2½ inches. The catalyst from Example 4 was calcined in place with an air flow of 10 cc/min at 1000° F. for 5 hours followed by a 10 minute nitrogen purge of 10 cc/min while the reactor temperature dropped to 700° F. The temperature distribution of the bed after passing charge for two hours is shown in Table 2. The effluent stream from the reactor was collected between 1 and 2 hours on stream. Run conditions and product analysis are shown in Table 3. In the run 72.2% of the methyl alcohol was converted of which 41.4% went to oxygen-free hydrocarbon product. The selectivity for ethylene was 59.7%.

TABLE 3

| | Example 4 | Example 5 |
|---|---|---|
| Charge: | MeOH | MeOH/H₂O |
| Hours on Stream | 2 | 2 |
| Temp., ° F (nominal) | 700 | 700 |
| WHSV (Total) | 2.0 | 3.6 |
| of MeOH | — | 1.2 |
| of Water | — | 2.4 |
| Mole Ratio (H₂O/MeOH) | — | 3.4/1 |
| Conversion of MeOH, wt. % | 88.2 | 72.2 |
| Product (wt. %) | | |
| DME | 36.9 | 3.9 |
| Water (excludes water in charge) | 40.3 | 54.7 |
| Hydrocarbon Phase | 22.4 | 41.4 |
| Hydrocarbon Phase (wt. %) | | |
| $C_1$ | 2.1 | 1.6 |
| $C_2=$ | 42.5 | 59.7 |
| $C_2$ | 0.4 | 1.1 |
| $C_3=$ | 26.1 | 23.6 |
| $C_3$ | 1.8 | 5.2 |
| $C_4=$ | 6.7 | 5.8 |
| $C_4$ | 3.8 | 1.3 |
| $C_5=$ | — | 1.4 |
| $C_5^+$ | 16.5 | 0.3 |

EXAMPLE 6

A synthetic offretite was prepared as follows:

Into a solution comprising 92 grams sodium aluminate, 112 grams sodium hydroxide, 277.6 grams potassium hydroxide and 1440 grams water were added 2142 grams colloidal silica sol and from a separate source, 131.2 grams of a 50% by weight aqueous tetramethylammonium chloride solution. The mixture was heated at about 212° F. and within 5 days crystals formed. The crystals were separated from the supernatant liquid, washed, dried and then calcined 96 hours at 900° F. in air. Chemical analysis of the product showed the following mole ratios:

$R_2O^{(1)}$ : 0.31
$Na_2O$ : 0.12
$K_2O$ : 0.63
$Al_2O_3$ : 1.0
$SiO_2$ : 7.9

(1) R = $(CH_3)_4N$ — tetramethylammonium.

This offretite was further processed by first heating at 1100° F. for 6 hours and then base exchanged with 2520 ml of 5% $NH_4Cl$ solution at 180° F. Four one hour contacts with fresh 5% $NH_4Cl$ solution were employed. The mixture of solution and offretite was stirred during the base exchange process. Following the base exchange treatment the offretite was then water washed free of chloride ion with 8 liters of water and air dried at 230° F. This material contained 0.06 weight percent sodium. A portion of this material was pelleted and sized to 14 × 25 mesh and then calcined in air for 10 hours at 1000° F. The adsorption properties of this material were determined. The product sorbed 9.7 weight percent cyclohexane determined at 25° C. and under a pressure of 20 mm Hg, 10.1 weight percent normal hexane determined at 25° C. and under a pressure of 20 mm Hg, and 21.9 weight percent water determined at 20° C. and 12 mm Hg.

EXAMPLE 7

Methanol at a rate of 3.8 ml per hour was passed over 1.0 gram of the catalyst of Example 6. The catalyst pretreatment and purge procedures are the same as described in Example 2. The run conditions, temperature profile of the bed and product analysis of the reactor effluent collected between 1 and 2 hours on stream are described in Table 4. Of the 82.8% methanol converted 2.4% went to oxygen-free hydrocarbon product. Ethylene was 20.2% of the hydrogen phase.

EXAMPLE 8

A charge solution comprised of 30% weight of methanol and 70 weight percent of water was passed over 3.0 grams of the acid offretite of Example 6 at a rate of 8.9 gram per hour at atmospheric pressure. The 15 mm outer diameter tubular glass reactor of Example 2 was used in this experiment. This experiment was run under conditions essentially identical to Example 2. Data are shown in Table 4. The methanol was 91.8% converted of which 40.4% went to oxygen-free hydrocarbon product of which 28.9% was ethylene. The ethylene yield per pass was 25 times greater than for Example 7.

EXAMPLE 9

A synthetic offretite was prepared by interacting the following solutions:

| Silicate solution: | Q-Brand | 960 g. |
|---|---|---|
| | KOH (88%) | 119.5 g. |
| | $H_2O$ | 1050 g. |
| Alum solution: | $Al_2(SO_4)_3 \cdot XH_2O$ | 100.5 g. |
| | KCl | 107 g. |
| | $H_2O$ | 550 g. |
| Tetramethylammonium chloride (50%) | | 128.6 g. |

The above silicate and alum solutions were mixed in a Waring blender for 10 minutes. The resultant gel was aged at ambient temperatures for four hours, then was transferred to a 1 gallon autoclave. TMA Cl was added to the gel. The mixture was crystallized at 210° F. with stirring for about 65 hours. The product mixture was filtered, washed and dried. The product was TMA offretite, as shown by x-ray diffraction pattern. The crystal size of the product was 0.040–0.2 micron. The chemical composition was found to be:

| | Weight Percent |
|---|---|
| $SiO_2$ | 72.2 |
| $Al_2O_3$ | 13.7 |
| Na | 0.64 |
| K | 5.4 |
| N | 0.87 |
| C | 4.76 |
| Ash | 87.5 |

The dried zeolite was precalcined at 1000° F. in flowing N for 3 hours, followed by $NH_4NO_3$ exchange to reduce Na content in zeolite. The sample was sized into 14/20 mesh and air calcined at 1000° F. for 3 hours. The final product was analyzed and found to contain 0.02% weight Na and 2.4% weight K.

EXAMPLE 10

One gram of the offretite described in Example 9 was used in an experiment in which methanol was passed over this material under conditions essentially identical to Example 7. Data are shown in Table 4. Of the 81.4% converted methanol 1.6% went to oxygen-free hydrocarbon product.

EXAMPLE 11

The methanol/$H_2O$ charge solution of Example 2 was passed over 2.0 grams of the catalyst of Example 9 at a rate of 7.8 ml per hour. The experimental procedure was the same as described in Example 2. Data are shown in Table 4. Of the 79.4% converted methanol 36.7% went to oxygen-free hydrocarbon product. Ethylene was 40.2% and propylene was 21.1% of this hydrocarbon product.

EXAMPLE 12

Synthetic tetramethylammonium offretite was prepared as follows:

Two solutions were made and interacted:
1. Alum Solution
   67.6 g Sodium aluminate
   102 g 50% TMACl (tetramethylammonium chloride)
   86.4 g NaOH (97.1%)
   213 g KOH (86.0%)
   1083 g $H_2O$
2. Ludox Colloidal Silica — 30 weight percent $SiO_2$ — 1557 g.

These two solutions were mixed together in a Waring Blendor for 10 minutes, transferred to polypropylene jar, and allowed to crystallize in a steam bath at 210°–212° F. The reaction required 42 hours to form a highly crystalline zeolite identified as TMA offretite.

The product was separated from the reaction mixture by filtration and washing, followed by drying at 230° F.

The analyzed product had the following composition:
Na, wt %: 0.95
K, wt %: 5.0
Al$_2$O$_3$, wt %: 13.8
SiO$_2$, wt %: 68.7

Molar ratios were:

0.15 Na$_2$O : 0.48 K$_2$O : 0.33 R$_2$O Al$_2$O$_3$ 8.42 SiO$_2$ where R = tetramethylammonium (TMA) ion.

The adsorption properties were:
Cyclohexane, wt %: 8.8
n-Hexane, wt %: 9.2
H$_2$O, wt %: 18.2

The above alkali zeolite was pre-calcined in N$_2$ for 3 hours at 1000° F., then base exchanged at room temperature with a 1 N NH$_4$NO$_3$ solution employing 10 ml/g of zeolite. The zeolite was contacted twice followed by water wash, air drying at 230° F., pelleting and sizing. The catalyst was finally calcined for 3 hours at 1000° F. prior to use in methanol conversion.

The final catalyst had a residual sodium content of 0.12 weight percent while the potassium content was 2.0 weight percent.

EXAMPLE 13

One gram of the TMA offretite of Example 12 was used in an experiment identical to Example 7. Data are shown in Table 4. The methanol was 83.2% converted of which 16.1% went to oxygen-free hydrocarbon product.

EXAMPLE 14

The charge solution of Example 2 was passed over 2.0 grams of the catalyst of Example 12 at a rate of 7.6 ml/hr. The experimental procedure was the same as described in Example 2. Data are shown in Table 4. Of the 95.5% methanol that was converted 42.7% went to oxygen-free hydrocarbon product. Ethylene was 32.7% and propylene was 15.2% of this hydrocarbon product.

EXAMPLE 15

Synthetic erionite was prepared by interacting the following solutions:

A. Sodium Aluminate Solution
  98.2 g NaAlO$_2$ (41.8 wt % Al$_2$O$_3$, 33.1 wt % Na$_2$O)
  1680 ml H$_2$O
  208 g NaOH 97 wt %
  42.4 g KOH 85.5 wt %
B. Colloidal Silica
  234 g Colloidal Silica 30 wt % SiO$_2$
C. Benzyltrimethyl Ammonium Chloride
  142 g 60 wt % solution These were mixed together adding C to A and then adding B. After mixing for 15 minutes the slurry was transferred to two polypropylene jars and reacted in a 212° F. bath for 68 days. The crystalline synthetic erionite product had the following composition:
Na, wt %: 2.3
K, wt %: 4.7
N, wt %: 0.77
Al$_2$O$_3$, wt %: 14.1
SiO$_2$, wt %: 81.0
Ash: 86.6

The adsorption capacity of a sample after calcination for 10 hours at 1000° F. was:
Cyclohexane, wt %: 1.0
n-Hexane, wt %: 8.4
H$_2$O: 16.6
m$^2$/g was 447

The zeolite prepared above was calcined for 10 hours at 1000° F. and then contacted 4 times with 113 ml of 0.5 N NH$_4$Cl solution at 190°–195° F. The exchanged zeolite was water washed essentially free of chloride ion, dried at 230° F., pelleted and sized 14–25 mesh and then calcined for 10 hours at 1000° F. prior to use. The residual sodium content was 0.18 weight percent.

EXAMPLE 16

Methanol at a rate of 7.6 ml per hour was passed over 2.0 grams of a synthetic erionite described in Example 15. The experimental procedure was the same as described in Example 7. Data are shown in Table 4. The methanol was 76.4% converted of which 6.1% went to oxygen-free hydrocarbon product.

EXAMPLE 17

A methanol/water charge solution as described in Example 2 was passed over 2.0 grams of the catalyst described in Example 15 at a rate of 7.8 ml per hour at atmospheric pressure. The experimental procedure was the same as described in Example 2. Data are shown in Table 4. Of the methanol converted (84.8%), 39.3% went to oxygen-free hydrocarbon product. The hydrocarbon product contained 60.1% ethylene and 25.9% propylene.

EXAMPLE 18

Zeolite T was prepared in accordance with Example 1 of U.S. Pat. No. 2,950,952. The resulting product had the following composition:
Na, wt %: 2.07
K, wt %: 8.18
Al$_2$O$_3$, wt %: 16.8
SiO$_2$, wt %: 67.7
Molar ratio of SiO$_2$/Al$_2$O$_3$: 6.8

The sorption capacity of a sample calcined at 1000° F. was as follows:
Cyclohexane, wt %: 0.9
n-Hexane, wt %: 2.0
H$_2$O, wt %: 12.6

The above alkali zeolite was subsequently processed by calcining in air for 10 hours at 1000° F. then exchanged for 2–4 hour contacts with 5 M NH$_4$Cl at 180° F. using 6 ml of solution per gram of zeolite. This treatment was followed by water washing essentially free of Cl ion, drying and recalcining for 10 hours at 1000° F. The base exchange step was repeated again to reduce the residual alkali to low level. The water washed exchanged zeolite was air dried at 230° F., pelleted and sized 14–25 mesh and recalcined for 10 hours at 1000° F.

An analysis of the final catalyst showed the following composition:
Na, wt %: 0.075
K, wt %: 1.65
Al$_2$O$_3$, wt %: 18.7
SiO$_2$, wt %: 78.8

Molar Ratio SiO$_2$/Al$_2$O$_3$ 7.2
The sorption capacity was as follows:
Cyclohexane, wt %: 0.6 n-Hexane, wt %: 5.7
H₂O, wt %: 13.1

Surface area was 199 m²/g

EXAMPLE 19

The catalyst used here was prepared by the method described in Example 18. Methanol at a rate of 7.5 ml/hr was passed over 2 grams of this catalyst under conditions essentially the same as described in Example 7. Data are shown in Table 4. Of the 69.1% converted methanol only 2% went to oxygen-free hydrocarbon product.

EXAMPLE 20

The catalyst sample used in Example 19 was removed from the reactor, placed in a crucible and calcined in air for 16 hours at 1000° F. It was placed back into the same reactor, heated up in nitrogen to 700° F. and a methanol/H₂O charge solution as described in Example 2 was passed over this 2.0 grams of catalyst at a rate of 7.4 ml per hour. The experimental procedure was similar to that described in Example 2. Data are shown in Table 4. Of the 33% methanol converted, 20.6% went to oxygen-free hydrocarbon product which was 54.4% ethylene and 25.9% propylene.

TABLE 4

| Example No. | 7 | 8 | 10 | 11 | 13 |
|---|---|---|---|---|---|
| Charge: wt % MeOH | 100 | 30 | 100 | 30 | 100 |
| wt % Water | — | 70 | — | 70 | — |
| Axial Length of Bed in inches | 1¾ | 1½ | 2¼ | 3½ | 2¼ |
| Reactor Diameter (mm OD) | 8 | 15 | 8 | 8 | 8 |
| Temp Profile 0 | 693 | 422 | 660 | 221 | 666 |
| Inches from ½ | 710 | 602 | 700 | 497 | 703 |
| top 1 | 703 | 696 | 700 | 649 | 706 |
| 1½ | 709 | 715 | 703 | 695 | 698 |
| 2 | 720 | — | 723 | 700 | 702 |
| 3 | — | — | — | 725 | — |
| Hrs. on Stream of Temp Profile | 2 | 2 | 2 | 2 | 2 |
| WHSV (MeOH + H₂O) | — | 4.5 | — | 3.5 | — |
| on MeOH | 2.8 | 1.0 | 2.8 | 0.82 | 2.9 |
| Mole Ratio: H₂O/MeOH in Charge (Calculations from Recovered) | — | 3.4/1 | — | 5.9/1 | — |
| Converted MeOH (wt %) | 82.8 | 91.8 | 81.4 | 79.4 | 83.2 |
| Products (charge free) -wt. % | | | | | |
| Water | 32.1 | 54.1 | 31.4 | 52.4 | 40.9 |
| DME | 65.3 | 5.6 | 65.8 | 10.9 | 42.9 |
| HC Phase | 2.4 | 40.4 | 1.6 | 36.7 | 16.1 |
| HC Phase Composition (wt. %) | | | | | |
| C₁ | 8.6 | 4.2 | 12.7 | 7.1 | 1.6 |
| C₂= | 20.2 | 28.9 | 19.8 | 40.2 | 13.1 |
| C₂ | 0 | 0.7 | 0 | 1.4 | 0 |
| C₃= | 20.2 | 18.1 | 18.6 | 21.1 | 16.4 |
| C₃ | 0 | 14.8 | 0 | 12.3 | 0 |
| C₄= | 16.8 | 6.5 | 14.8 | 6.0 | 10.9 |
| C₄ | 20.9 | 8.0 | 20.5 | 9.1 | 9.0 |
| C₅+ | 12.6 | 18.8 | 12.4 | 2.5 | 48.9 |

| Example No. | 14 | 16 | 17 | 19 | 20 |
|---|---|---|---|---|---|
| Charge: wt % MeOH | 30 | 100 | 30 | 100 | 30 |
| wt % Water | 70 | — | 70 | — | 70 |
| Axial Length of Bed in inches | 4 | 3½ | 3½ | 1¾ | 1¾ |
| Reactor Diameter (mm OD) | 8 | 8 | 8 | 15 | 15 |
| Temp Profile 0 | 225 | 646 | 265 | 642 | 593 |
| Inches from ½ | 531 | 650 | 522 | 698 | 698 |
| top 1 | 660 | 697 | 650 | 701 | 699 |
| 1½ | 695 | 713 | 688 | 705 | 700 |
| 2 | 700 | 706 | 690 | 717 | 726 |
| 3 | 728 | 723 | 723 | — | — |
| Hrs. on Stream of Temp Profile | 2 | 2 | 2 | 2 | 2 |
| WHSV (MeOH + H₂O) | 3.4 | — | 3.5 | — | 3.3 |
| on MeOH | 0.69 | 2.8 | 0.93 | 2.6 | 0.83 |
| Moles Ratio: H₂O/MeOH in Charge (Calculations from Recovered) | 7.1/1 | — | 5/1 | — | — |
| Converted MeOH (wt %) | 95.5 | 76.4 | 84.8 | 69.1 | 33.0 |
| Products (charge free) -wt. % | | | | | |
| Water | 56.1 | 35.8 | 53.4 | 34.4 | 41.4 |
| DME | 1.2 | 58.0 | 7.3 | 63.2 | 37.9 |
| HC Phase | 42.7 | 6.1 | 39.3 | 2.0 | 20.6 |
| HC Phase Composition (wt. %) | | | | | |
| C₁ | 5.6 | 3.6 | 1.7 | 2.1 | 4.7 |
| C₂= | 32.7 | 45.7 | 60.1 | 40.5 | 54.4 |
| C₂ | 1.0 | 0.7 | 1.9 | 0 | 8.5 |
| C₃= | 15.2 | 30.0 | 25.9 | 22.1 | 25.9 |
| C₃ | 23.4 | 0 | 3.6 | 0 | 0 |
| C₄= | 6.4 | 10.0 | 4.0 | 7.4 | 3.9 |
| C₄ | 12.6 | 6.5 | 1.2 | 22.9 | 1.5 |
| C₅+ | 3.0 | 3.1 | 1.2 | 4.6 | 1.1 |

EXAMPLE 21

This catalyst was prepared by calcining 243 grams of natural erionite (crushed and ground ore of Jersey Valley, Nev.) in a thin layer at 1200° F. in a furnace. The calcined material was then exchanged at reflux temperature of 218° F. with 1200 ml. of 5 Molar NH₄Cl solution per exchange. Two 2-hour exchanges were used followed by a wash with 2000 ml. of water after the second exchange.

The resulting wet cake was reslurried in 435.8 grams of 8.3 weight percent Ca(NO₃)₂ solution for 2 hours at 180° F., followed by filtering, drying at 225°–250° F., and recalcining for 1½ hours in a thin layer at 1200° F. in a preheated furnace.

The recalcined catalyst was then re-exchanged for 2 hours at a reflux temperature of 216° F. with 1200 ml. of 5 Molar NH₄Cl solution and washed with 2000 ml. of water.

A sample of the above hydrogen form of erionite was dried at 230° F. for 22 hours, pelleted and sized 14–25 mesh, followed with a calcination at 1000° F. for 10 hours. This catalyst was used in evaluation of methanol conversion with and without added water under the conditions set forth in Table 5.

EXAMPLE 22

In preparing the zinc form of the natural erionite described in the preceding Example, 73.4 grams of the above ammonium form as wet cake was slurried with 67 ml. of water and heated to 190° to 195° F. To this was added 116 ml. of 2 Normal Zn(NO₃)₂ solution at 190°–195° F. The contact was continued for 4 hours at 210° F., followed by filtering, washing with 500 ml. of water, drying at 225–250° F., pelleting and sizing to 14–25 mesh. The sized zinc erionite product was calcined at 1000° F. prior to use in methanol conversion with and without added water. The conversion conditions and results obtained are set forth in Table 5 below.

TABLE 5

| | Catalyst of Example 21 | | Catalyst of Example 22 | |
|---|---|---|---|---|
| Length of Bed (Inches) | 2¾ | 1¼ | 1¾ | 3½ |
| Temp ° F (inches from 0 | 673 | 600 | 691 | 438 |
| top of bed) ½ | 701 | 680 | 700 | 648 |
| 1 | 710 | 711 | 701 | 698 |
| 1½ | 707 | — | 717 | 702 |
| 2 | 722 | — | — | 704 |
| Hours on stream for temp profile | 2 | 2 | 2 | 2 |

TABLE 5-continued

| | Catalyst of Example 21 | | Catalyst of Example 22 | |
|---|---|---|---|---|
| WHSV Total | — | 3.4 | — | 3.4 |
| MeOH | 2.8 | 1.0 | 2.6 | 0.8 |
| Water | — | 2.4 | — | 2.6 |
| Converted Charge (wt. %) (excludes water) | 49.0 | 40.9 | 64.8 | 31.0 |
| Product (excludes charge) | | | | |
| DME | 62.6 | 37.2 | 63.8 | 41.4 |
| Water | 32.2 | 41.7 | 35.2 | 40.0 |
| Hydrocarbon Phase | 4.5 | 21.1 | 0.9 | 18.6 |
| Hydrocarbon Distribution (wt. %) | | | | |
| $H_2$ | 0.6 | — | 2.5 | — |
| $C_1$ | 2.8 | 2.8 | 11.2 | 2.3 |
| $C_2=$ | 36.7 | 51.6 | 54.8 | 53.1 |
| $C_2$ | 0.9 | 3.6 | 0 | 2.0 |
| $C_3=$ | 33.0 | 32.7 | 23.5 | 27.5 |
| $C_3$ | 0 | 0 | 0 | 2.8 |
| $C_4=$ | 11.4 | 5.5 | 0 | 1.7 |
| $C_4$ | 8.4 | 2.1 | 8.1 | 9.3 |
| $C_5$ | 6.1 | 1.7 | 0 | 1.3 |

It will be seen from the above examples that while ZSM-34 was a very effective catalyst for selectively converting methanol to $C_2$-$C_3$ olefins, its selectivity was markedly improved by the presence of added water to the methanol feed.

It is further to be noted that methanol was converted only slightly over two different samples of synthetic offretite (Examples 7 and 10). The oxygen-free hydrocarbon product though small contained reasonable ethylene concentrations, e.g. 20.2 percent for Example 7. A third offretite sample gave a higher yield of oxygen-free hydrocarbon product with a somewhat diminished (13.1 percent) ethylene concentration (Example 13).

When a mixture of water (70%) and methanol (30%) was passed over these offretite samples under conditions of equal residence times, (total moles of charge per minute, i.e. water plus methanol, divided by volume of catalyst bed) ethylene/propylene yields increased markedly (Examples 8, 11 and 14). The relative increase in selectivity for producing ethylene per pass for these three samples are shown below.

| A. $CH_3OH$ Over Offretite | B. $CH_3OH + H_2O$ Over Offretite | Relative Increase In $C_2=$ Selectivity Per Pass B ÷ A |
|---|---|---|
| Example 7 | Example 8 | 27 |
| Example 10 | Example 11 | 45 |
| Example 13 | Example 14 | 8 |

In each instance, the improved selectivity factor is quite large.

The same trend was observed for synthetic erionite. The improvement in ethylene selectivity per pass increased 9 times in going from no water (Example 16) to water dilution (Example 17). Similar trend was observed for Zeolite T prepared in Example 18. The improvement in ethylene selectivity using this zeolite increased sixfold in going from no water (Example 19) to water dilution (Example 20).

It is to be understood that the foregoing description is merely illustrative of preferred embodiments of the invention of which many variations may be made by those skilled in the art within the scope of the following claims without departing from the spirit thereof.

We claim:

1. A catalytic process for converting an organic charge consisting essentially of methanol, dimethyl ether or mixtures thereof, together with at least about 0.25 moles of water per mole of said organic charge, to a hydrocarbon product rich in ethylene and propylene which comprises contacting said charge under conversion conditions including a temperature between about 500° F. and about 1000° F., a pressure from about 0.1 to 30 atmospheres and a weight hourly space velocity of between about 0.1 and about 30 with a catalyst comprising a crystalline aluminosilicate zeolite of the erionite-offretite family.

2. The process of claim 1 wherein ethylene and propylene constitute a major proportion of the hydrocarbon reaction product.

3. The process of claim 2 wherein the ethylene content of said product exceeds the propylene content.

4. The process of claim 1 wherein said organic charge consists essentially of methanol.

5. The process of claim 1 wherein the amount of water added is greater than about 0.5 moles per mole of said organic charge.

6. The process of claim 1 wherein unconverted methanol or dimethyl ether and at least part of the water in the product is recycled to the reaction zone.

7. The process of claim 1 wherein said crystalline aluminosilicate has been thermally treated at a temperature of from about 200° C. to about 750° C.

8. The process of claim 7 wherein at least 10 percent of the cationic sites of said crystalline aluminosilicate zeolite are occupied by ions other than alkali or alkaline earth metals.

9. The process of claim 8 wherein said ions are hydrogen, hydrogen precursor or combinations thereof.

10. The process of claim 1 wherein said crystalline aluminosilicate zeolite is predominately in the hydrogen form.

11. The process of claim 1 wherein said crystalline aluminosilicate zeolite is contained in a matrix therefor.

12. The process of claim 1 wherein said crystalline aluminosilicate zeolite is erionite.

13. The process of claim 1 wherein said crystalline aluminosilicate zeolite is offretite.

14. The process of claim 1 wherein said crystalline aluminosilicate zeolite is zeolite T.

15. The process of claim 1 wherein said crystalline aluminoslicate zeolite is ZSM-34.

16. The process of claim 8 wherein said crystalline aluminosilicate zeolite is erionite.

17. The process of claim 8 wherein said crystalline aluminosilicate zeolite is offretite.

18. The process of claim 8 wherein said crystalline aluminosilicate zeolite is zeolite T.

19. The process of claim 8 wherein said crystalline aluminosilicate zeolite is ZSM-34.

* * * * *